United States Patent [19]
Heller et al.

[11] Patent Number: 5,827,736
[45] Date of Patent: Oct. 27, 1998

[54] PURIFIED AND ISOLATED SEROTOLI CELL-SECRETORY CELL HYBRID

[75] Inventors: Richard Heller, Brandon; Don F. Cameron, Lutz; Paul R. Sanberg, Spring Hill; Mark J. Jaroszeski, Tampa, all of Fla.

[73] Assignee: University of South Florida, Tampa, Fla.

[21] Appl. No.: 782,509

[22] Filed: Jan. 9, 1997

Related U.S. Application Data

[63] Continuation of Ser. No. 425,868, Apr. 20, 1995, abandoned.

[51] Int. Cl.$^6$ .............................. C12N 15/00; C12N 5/00; C12N 5/02
[52] U.S. Cl. .................. 435/346; 435/172.2; 435/285.2; 435/366
[58] Field of Search .................................... 435/346, 347, 435/325, 366, 285.2, 172.2

[56] References Cited

U.S. PATENT DOCUMENTS

| | | | |
|---|---|---|---|
| 4,195,125 | 3/1980 | Wacker | 435/172.2 |
| 4,441,972 | 4/1984 | Pohl | 435/172.2 |
| 4,455,296 | 6/1984 | Hansen et al. | 424/150.1 |
| 4,476,004 | 10/1984 | Pohl | 435/285.2 |
| 4,578,168 | 3/1986 | Hofmann | 435/285.2 |
| 4,822,470 | 4/1989 | Chang et al. | 435/172.2 |
| 4,955,378 | 9/1990 | Grasso | 607/53 |
| 5,017,378 | 5/1991 | Turner et al. | 424/422 |
| 5,082,670 | 1/1992 | Gage et al. | 424/520 |
| 5,262,055 | 11/1993 | Bae et al. | 210/645 |
| 5,304,603 | 4/1994 | Cheng et al. | 514/12 |

FOREIGN PATENT DOCUMENTS

WO9528167 of 1995 WIPO.

OTHER PUBLICATIONS

Bardin et al., The Sertoli Cell. In: *The Physiology of Reproduction*, Knobil, E. and J. Neill (eds). Raven Press, Ltd., New York, pp. 933–947. (1988).

Jaroszeski et al., "Mechanically facilitated cell–cell electrofusion" *Biophys. J.* 67:1574–1581 Oct. (1994).

Jaroszeski et al., "Detection and Quantitation of cell–cell electrofusion products by flow cytometry" *Anal. Biochem.* 216:271–275 (1994).

Lo, M.M.S. et al., "Monoclonal antibody production by receptor–mediated electrically induced cell fusion " *Nature* 310:794–796 Aug. (1984).

Pakzaban et al., "Increased proportion of Ache–rich zones and improved morphological integration in host striatum of fetal . . . " *Exp. Brain Res.* 94:13–22 (1993).

Selawry and Cameron, "Sertoli cell–enriched fractions in successful islet cell transplantation" *Cell Transplan.* 2:123–129 (1993).

Cameron et al., "Successful islet/abdominal testis transplantation does not require leydig cells" *Transplantation,* vol. 50, 649–653, No. 4, (Oct. 1990).

Carson et al., "Synthesis and secretion of a novel binding protein for retinol by a cell line derived from Sertoli Cells" *Journal of Biological Chemistry,* vol. 259, No. 5, pp. 3117–3123 (1984).

*Primary Examiner*—Leon B. Lankford, Jr.
*Assistant Examiner*—Christopher R. Tate
*Attorney, Agent, or Firm*—Kohn & Associates

[57] ABSTRACT

A purified and isolated Sertoli cell and secretory cell hybrid, or an aggregate of these two cells, wherein the secretory cells preferably are pancreatic islet cells and chromaffin cells characterized by being a) capable of survival in situ after transplantation;

b) able to provide immunoprotection for the hybrid cells when transplanted; and c) able to provide a mechanism for prolonged viability and cellular functionality of the transplanted hybrid cells wherein the hybrid maintains both the immunoprotection characteristics of the Sertoli cell and the secretory function of the secretory cell.

4 Claims, 2 Drawing Sheets

PURIFIED AND ISOLATED SEROTOLI CELL-SECRETORY CELL HYBRID

This application is a continuation of application Ser. No. 08/425,868 filed on Apr. 20, 1995, now abandoned.

TECHNICAL FIELD

The present invention relates to the field of fused or aggregated cells having desired functional and immunological capabilities and the use of such cells.

BACKGROUND ART

Advances in cell fusion technology have allowed for cell fusion to become an important tool in biotechnology. For example, one key procedure in genetic engineering is the introduction of exogenous genetic material into a desired host cell. The insertion can be accomplished by various means and techniques. Cell fusion is also important in the production of monoclonal antibodies. Specifically, the monoclonal antibodies can be produced by the fusion of antibody producing cells with continuously dividing cancer cells. (Galfre, G. et al., 1977; Lo, M.M.S. et al., 1984). Conventional cell fusion techniques are summarized in U.S. Pat. No. 4,822,470 to Chang, issued Apr. 18, 1989. Methods of using an apparatus for cell poration and cell fusion are disclosed in the Chang patent as well as the U.S. Pat. No. 4,955,378 to Grasso, issued Sep. 11, 1990, although these disclosures are not exhaustive of the state of the art.

From the above mentioned prior art, it can be concluded that it is no longer a novel concept to generally combine two cells having different functions resulting in a fused cell or hybrid capable of the combined functions of the two precursor cells.

The present invention relates to utilizing the aforementioned technology with regard to problems related to, for example, insulin dependent diabetes. A major problem is immunologic rejection of transplanted cells. It has recently been shown that if you co-transplant with Sertoli cells, the graft would avoid immune rejection and survive indefinitely. Insulin-dependent diabetes is a major health problem throughout the world for which a cure is not yet available. A desirable approach to alleviating the complications of this disease is to provide the patient with an endogenous insulin. This can be accomplished through the transplantation of insulin-secreting cells (islet cells).

There are several major difficulties in cell transplantation in general and in the transplantation of islet cells in specific. Major difficulties with regard to islet cell transplantation are the lack of allografts and the inevitable rejection of allograft substitutes (xenografts).

In order to avoid transplantation rejection, the state of the art methodology is to use systemically delivered immunosuppressant therapy. However, this renders patients susceptible to many infectious agents, the infectious agents often times being more life threatening than the disease itself. Accordingly, it is desirable to alleviate this major problem by creating local immunosuppression at the transplantation site, thereby obviating the need for systemic immunosuppressant therapy.

Recently, it has been demonstrated that pancreatic islet cells can be successfully transplanted at sites where they were typically rejected if grafted with Sertoli cells isolated from the testis. Islet cells of the Sertoli-islet grafts also maintained their ability to secrete insulin in response to the usual stimuli. Formerly diabetic rats became normoglycemic within twenty-four hours of transplantation (Selawry and Cameron, 1993).

Although the aforementioned cell co-transplantation protocol was successful, the procedure is limited by the difficult nature of primary cell isolation between both Sertoli cells and islet cells. In addition, there are related complications in maintaining a close association of the two cell types.

The unique mechanism of graft survival appears primarily dependent upon the secretion of immunosuppressant factors by the Sertoli cells at the site of transplantation. Therefore, separation of the two cell types following transplantation would result in the rejection of the islet cells and return the animal to the diabetic state.

In view of the above, it is desirable to produce cell hybrids for use in the treatment of various diseases wherein the hybrids function both as a secretory cell to perform a specific desired function, such as either a curative function, supplemental function, or inhibitory function, in conjunction with the ability of performing an immuno-protective function of the same cells. More specifically, it would be desirable to produce transplantable insulin producing islet cell hybrids to be used in the treatment of insulin-dependent diabetes which also effectively avoid immune surveillance in a manner similar to the Sertoli cell-islet cell co-transplants described above.

SUMMARY OF THE INVENTION

In accordance with the present invention, there is provided a purified isolated Sertoli cell-secretory cell hybrid characterized by being a) capable of survival in situ after transplantation;

b) able to provide immunoprotection for the hybrid cells when transplanted; and c) able to provide a mechanism for prolonged viability and cellular functionality of the transplanted cells wherein the hybrid maintains both the immunoprotection characteristics of the Sertoli cell and the secretory function of the secretory cell.

There is also provided in accordance with the present invention, a purified and isolated cell hybrid comprising a hybrid of a secretory cell and an immunoprotective cell; the hybrid being a) able to survive in situ after transplantation;

b) able to maintain a secretory function in response to in situ stimuli; and c) able effectively invoiding in situ immune surveillance.

BRIEF DESCRIPTION OF THE FIGURES

Other advantages of the present invention will be readily appreciated as the same becomes better understood by reference to the following detailed description when considered in connection with the accompanying drawings wherein.

Figure 1:
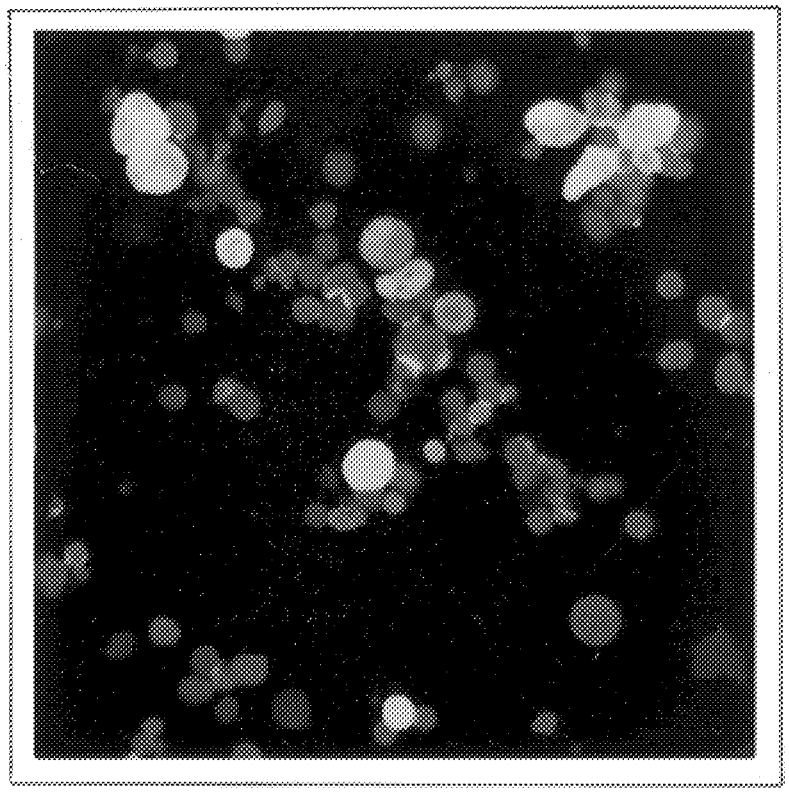
FIG. 1 is a fluorescent light photomicrograph of cells following electrofusion, unfused cells are stained red and green and fused hybrid cells appear yellow.

and intral-islet B cells (B) can be seen to better advantage, lower inset: at higher magnification/resolution, this electron micrograph illustrates a B cell (B) with characteristic insulin secretory granules.

DETAILED DESCRIPTION OF THE INVENTION

In accordance with the present invention, a purified and isolated cell hybrid is provided. The cell hybrid is characterized by being capable of survival in situ after transplantation, able to maintain a secretory function in response to in situ stimuli, and effectively avoiding in situ immune surveillance.

More specifically, the purified isolated cell hybrid is produced either as a hybrid and/or aggregate of separate cells in culture. As described above with regard to the prior art, both transplantation of Sertoli cells and secretory cells have resulted an effective treatment of insulin-dependent diabetes. The present invention utilizes what is termed a "cell hybrid" of the Sertoli cells and secretory cells to produce an effective treatment for certain diseases such as insulin-dependent diabetes or Parkinson's disease while also alleviating the problems caused by separation of the two cell types following transplantation.

Aggregation of the cells can be accomplished by means well known in the art. For example, cell fusion can be accomplished pursuant to the methods disclosed in the U.S. Pat. No. 4,822,470 to Chang, issued Apr. 18, 1989, those methods being incorporated herein by reference. Likewise, the methods disclosed in the U.S. Pat. No. 4,441,972 to Pohl, issued Apr. 10, 1984, can also be used. Both prior art patents disclose methods for fusing neutral polarizable biological bodies and sorting the bodies by exposing them to a non-uniform electric field. Both reference disclose the effective use of such methods, such as in producing antibody-producing hybrids and the combination of antibody-producing cells and cancer cells.

By being capable of survival, in situ after transplantation, the cell hybrids must thrive and also avoid in situ immune surveillance. Sertoli cells are nutritive supplying cells. (Bardin et al., 1988) Accordingly, the Sertoli cells, as part of the cell aggregate/hybrid, provide a nutritive effect for the aggregate/hybrid cells thereby increasing their survival. Survival after transplantation requires mechanisms for effectively avoiding in situ immuno-surveillance. Following transplantation, Sertoli cells have been shown to produce such an effect in situ, as demonstrated in the Selawry and Cameron (1993) reference set forth above. Hence, a combination of Sertoli cells with other cell types, such as islet cells, as a cell hybrid provides a transplantable three-dimensional aggregate capable of maintaining the hybrid's functional characteristics such as secreting insulin and effectively avoiding immunological rejection.

In a preferred embodiment of the present invention produced in accordance with the present invention, a purified and isolated islet cell hybrid is provided. The islet cell aggregate is characterized by being capable of survival in situ after transplantation, able to produce insulin in situ, and the production of insulin being controllable by in situ demand for insulin.

More specifically, the purified isolated islet cell hybrid is produced either as a hybrid or aggregate of separate cells in culture. As described above with regard to the prior art, both transplantation of Sertoli cells and islet cells have resulted an effective treatment of insulin-dependent diabetes. Critical to the effectiveness and utility of the cell hybrids is the maintenance of the functions of the component cells of the cell hybrids. For example, for diabetes, the cell hybrids must be able to produce insulin in situ while the production of insulin remains controllable by in situ demand for insulin. That is, the cell hybrids must be glucose sensitive and react accordingly to the production or non-production of insulin. Hence, the present invention provides transplantable cell hybrids able to produce insulin to produce a curative effect wherein the cells are regulatable in situ to provide an appropriate curative and maintenance effect.

In view of the above, the present invention more broadly provides a cell aggregate which can be, for example, a hybrid resulting from the combination of an immuno-protective cell (Sertoli cell) and a secretory cell, such as an insulin-producing cell, other secretory cells which can produce hormones, or regulatory compounds. Such hybrids, as demonstrated by the experimental section below, are capable of both in situ survival after transplantation and maintaining secretory function in response to in situ stimuli. By effectively avoiding in situ surveillance, these cells can be utilized for various curative, diagnostic, and maintenance providing functions.

Examples of secretory cells useful with regard to the present invention are chromaffin cells (Parkinson's Disease). It should be understood that the secretory function can include both naturally occurring products as well as engineered products.

Transplantation protocol can follow the procedure as described in Pakzaban et al., (1993) which can include infusing the cell hybrid into a target site.

As stated above, the present invention provides significant utility as a therapeutic agent. The present invention can also be utilized in vitro as a cell culture of extended life secretory cells which can be used as a test system for various therapeutic agents. For example, a preferred embodiment of the present invention which provides the islet cell hybrid which can be used for testing various diabetic treatments solely with regard to their effect on islet cells by use of the present system. Such a method would include the steps of providing a cell culture, adding a drug to be tested, and then monitoring the response of the cells. This type of test system is a well known method in the art. Such a system would utilize the nutritive effects of the Sertoli cells to decrease the nutrient requirements of the ongoing cell culture as well as to provide a biologically nourishing environment for the test cells.

The following experimental section illustrates the method of making and utilizing the present invention. Also, the following experiments clearly demonstrate the utility of the present invention and an in vitro and in vivo system.

EXPERIMENTAL SECTION

Cell—Cell Electrofusion:

A pulse generator (Model T800, BTX, San Diego, Calif.) can be used to deliver the electrical energy required to induce fusion. Pulses can be monitored using a digital storage oscilloscope with a custom written software package to analyze waveforms captured by the oscilloscope. The apparatus required to induce cell—cell contact can be a chamber developed in our laboratory (Jaroszeski et al., "Mechanically facilitated cell—cell electrofusion" *Biophys. J.* 67:1574–1581 Oct. 1994). Electrofusion of the different cell pairings can be achieved in the chamber using our standard protocol. Briefly, the chamber consists of two electrodes contained in a plexiglass housing to support and align the electrodes and to allow the distance between the electrodes to be precisely calibrated. One cell type from each of the cell pairings can be deposited, using a vacuum, onto a polycarbonate track etch membrane (Poretics Corporation, Livermore, Calif.) and placed over the face of the anode. Similarly, the other cell type can be deposited onto the face of the cathode. The layers of cells on each membrane can be contacted with each other by moving the electrode faces to a precisely calibrated distance at which time fusogenic direct current pulses will be administered. Pulse parameters are identified to provide maximum yields of hybrid cells.

Figure 2:
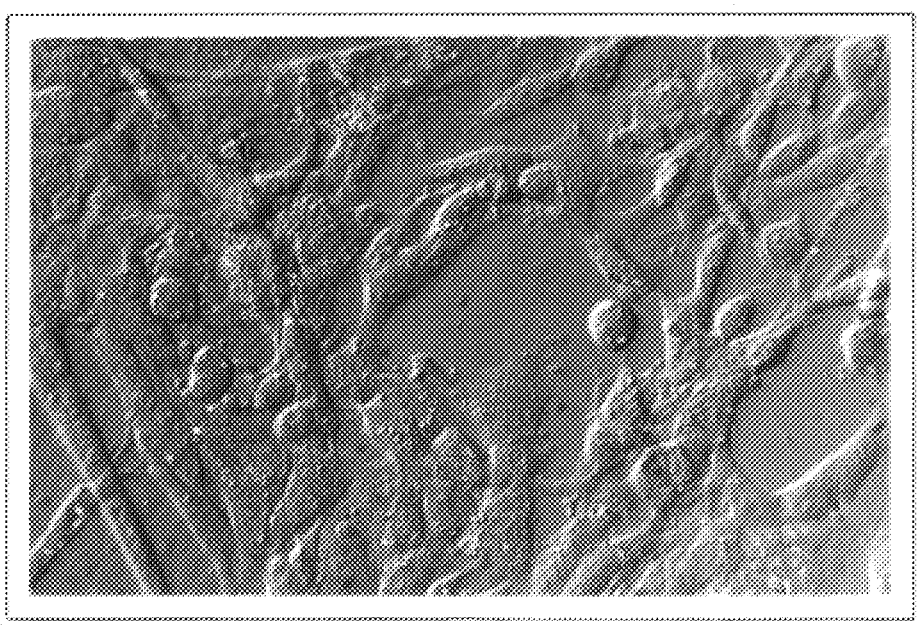
FIG. 2 is a light photomicrograph of hybrid cells in vitro derived from mouse TM4 cells and rat Sertoli cells.
Figure 3:
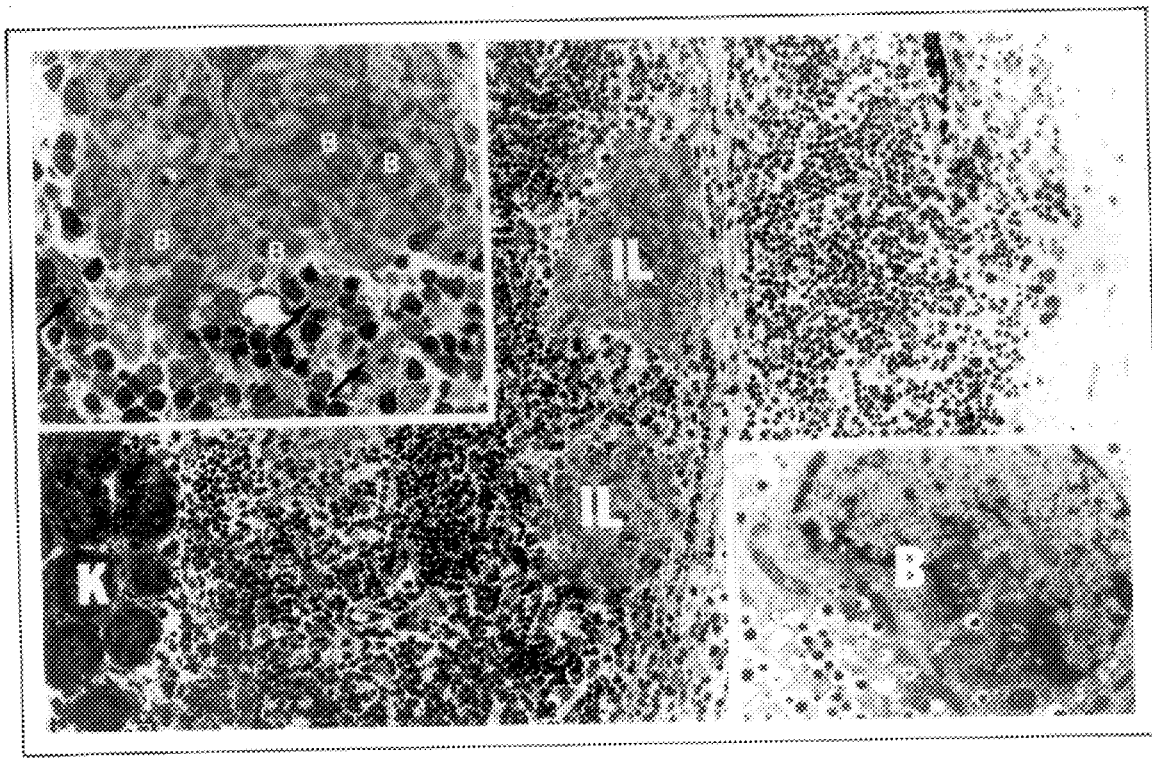
FIG. 3 is a light photomicrograph which illustrates the subcapsular region of a grafted rat kidney, normal kidney parenchyma (K) is observed along with two normal appearing pancreatic islets (IL), upper inset: at higher magnification, the distinctive structure of Sertoli cells with characteristic irregular nuclear profiles and nucleoli (arrows)

Detection and Quantitation of Fusion Products:

Detection and quantitation of fusion produces can be achieved using a method developed by our research group and described in the publication (Jaroszeski et al., 1993). The method utilizes flow cytometry in conjunction with two different vital fluorescent dyes. One fusion partner will be stained with 5-chloromethylfluorescein diacetate (CMFDA) and the other will be stained with 5-(and 6-)-4chloromethylbenzoyl amino tetramethylrhodamine (CMTMR). Cell staining is conducted prior to electrofusion. After fusion, cells that are composed of at least one fusion partner of each type will exhibit the fluorescence of both dyes (dual fluorescence) as shown in FIG. 1. Further, as shown in FIG. 2, hybrid cells in vitro derived from mouse TM4 cells (Sertoli cell line) and rat Sertoli cells were constructed and detected as described herein. Detection and quantitation of fusion products can be conducted using a Becton Dickinson FACStar Plus flow cytometer with an 80 mW argon laser tuned to a wavelength of 488 nm. The FL1 (green) cytometer channel can be used to detect CMFDA emission; CMTMR emission is detected in the FL1 (red) channel. Hybrid cells can be sorted based on FL1 vs. FL2 dot plots. Cells that exhibit dual fluorescence can be sorted and collected for subsequent growth and characterization. Referring to FIG. 3, the results of an in vivo experiment are shown. This Figure illustrates the subcapsular region of a grafted rat kidney. Normal parenchyma (K) was observed along with two normal appearing pancreatic islets (IL). The distinctive structure of Sertoli cells with characteristic irregular nuclear profiles and nucleoli (arrows) and intral-islet B cells (B) is also shown in this Figure. At higher magnification, a B cell with characteristic insulin secretory granules is visible. This figure illustrates that the Sertoli cell-islet cell hybrid constructed as described herein, survived grafting into a rat kidney.

The above data demonstrates the methods of making, utilizing, and utility of the present invention in in vivo and in vitro systems.

Throughout this application various publications are referenced by citation or number. Full citations for the publications referenced by number are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

REFERENCES CITED

Bardin et al., The Sertoli Cell. In: *The Physiology of Reproduction*, Knobil, E. and J. Neil (eds). Raven Press, Ltd., New York, pp. 933–947.

Galfre, G., *Nature* 266:550–552 (1977).

Jaroszeski et al., "Mechanically facilitated cell—cell electrofusion" *Biophys. J.* 67:1574–1581.

Jaroszeski et al., "Detection and Quantitation of cell—cell electrofusion products by flow cytometry" *Anal. Biochem.* 21 6:271–275 (1993).

Lo, M.M.S. et al., *Nature* 310:794–796 (1984).

Pakzaban et al., "Increased proportion of Ache-rich zones and improved morphological integration in host striatum of fetal . . . " *Exp. Brain Res.*, 97:13–22 (1993).

Selawry and Cameron, "Sertoli cell-enriched fractions in successful islet cell transplantation" *Cell Transplan.* 2:123–129 (1993).

What is claimed is:

1. A purified and isolated Sertoli cell-secretory cell hybrid which a) survives in situ after transplantation;

b) provides immunoprotection for the hybrid cells when transplanted; and c) provides a mechanism for prolonged viability and cellular functionality of the transplanted cells wherein the hybrid maintains both the immunoprotection characteristics of the Sertoli cell and the secretory function of the secretory cell selected from the group consisting of islet cells and chromaffin cells.

2. A cell hybrid as set forth in claim 1 wherein said hybrid cells are formed by electrofusion.

3. A cell hybrid as set forth in claim 1 wherein said secretory cells are islet cells.

4. A purified and isolated Sertoli cell-chromaffin cell fusion hybrid which a) survives in situ after transplantation into the central nervous system due to Sertoli-induced immunoprotection for the hybrid cell when transplanted; and c) provides the secretory function of the chromaffin cell.

* * * * *